United States Patent [19]

Epps et al.

[11] Patent Number: 4,670,436
[45] Date of Patent: Jun. 2, 1987

[54] HYPOGLYCEMIC 5-SUBSTITUTED PYRROLIDINYLIDENE COMPOUNDS, COMPOSITIONS AND USE

[75] Inventors: Joyce E. Epps, Jeffersonville; Kung-Tat Ng, Telford; Robert W. Tuman, Chalfont; Wu-Nan Wu, Landsdale, all of Pa.

[73] Assignee: McNeilab, Inc., Fort Washington, Pa.

[21] Appl. No.: 902,348

[22] Filed: Aug. 29, 1986

[51] Int. Cl.$^4$ .................. C07D 295/12; A61K 31/535
[52] U.S. Cl. .................................... 514/237; 544/141
[58] Field of Search .......................... 544/141; 514/237

[56] References Cited

U.S. PATENT DOCUMENTS 4,211,867 7/1980 Rasmussen .......................... 544/141

Primary Examiner—Robert W. Ramsuer
Attorney, Agent, or Firm—David J. Levy

[57] ABSTRACT

Pyrrolidinylidene compounds substituted at the 5-position of the following formula (I):

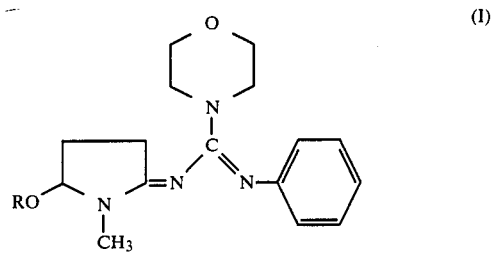

wherein R=H, alkyl or alkanoyl, and their use as hypoglycemic agents, e.g. in the treatment of diabetes, in a manner similar to linogliride.

9 Claims, No Drawings

HYPOGLYCEMIC 5-SUBSTITUTED PYRROLIDINYLIDENE COMPOUNDS, COMPOSITIONS AND USE

BACKGROUND OF THE INVENTION

Linogliride is an effective hypoglycemic agent used in the treatment of diabetes as described in U.S. Pat. No. 4,211,867. Chemical names of linogliride include N-(1-methyl-2-pyrrolidinylidine)-N'-phenyl-4-morpholinecarboximidamide and N-(1-methyl-2-pyrrolidinylidene)-N'-phenyl-4-morpholinecarboxamidine, the chemical structure being as follows:

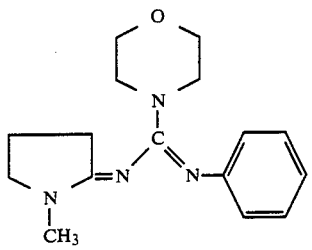

It is an object of the present invention to provide hypoglycemic agents having about equal or better efficacy compared to linogliride and which may have lessened side effects.

SUMMARY OF THE INVENTION

Pyrrolidinylidenes of the following formula (I):

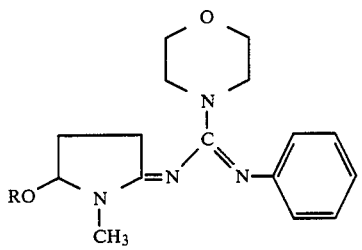

where R is hydrogen, alkyl or alkanoyl, as well as acid addition salts thereof for the treatment of diabetes in mammals such as humans.

DETAILED DESCRIPTION OF THE INVENTION

A 5-substituted pyrrolidinylidene of the following formula (I):

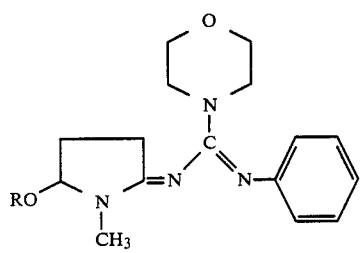

wherein R is hydrogen, alkyl or alkanoyl, and the pharmaceutically acceptable acid addition salts thereof.

In particular, R is hydrogen; alkyl, e.g. straight or branched chain of about 1 to 10 carbons such as methyl, ethyl or n-octyl; or alkanoyl; e.g. straight or branched chain alkyl of about 2 to 10 carbons such as acetyl, propionyl or n-octanoyl.

Particular compounds of the present invention are those of formula (I) where R is hydrogen, methyl, ethyl or acetyl.

Due to the presence of basic nitrogen in the compounds of formula (I), acid addition thereof are readily obtained and such pharmaceutically acceptable salt are included within the scope of this invention. The subject compounds (I) may be converted to their therapeutically active nontoxic acid addition salt form by treatment with an appropriate acid, such as, for example, an inorganic acid, such as hydrohalic acid, e.g. hydrochloric, hydrobromic and the like, and sulfuric acid, nitric acid, phosphoric acid and the like, or an organic, acid, such as, for example, acetic, propionic, glycolic, pamoic, pyruvic, malonic, succinic, maleic, fumaric, malic, tartaric, citric, benzoic, cinnamic, mandelic, methanesulfonic, ethanesulfonic, benzenesulfonic, p-toluenesulfonic, cyclohexanesulfamic, salicylic, p-aminosalicylic and the like acids. Conversely, the salt form can be converted by treatment with alkali into the free base form.

To prepare compounds of formula (I), one may obtain the compound wherein R is hydrogen as a metabolite from urine after administration of linogliride to a mammal, particularly a dog. Recovery may be by conventional techniques as described in Abstract No. 1683 of Federation Proceedings, Volume 45, No. 3, Mar. 1, 1986 issued at the 70th Annual Meeting of the Federation of American Societies for Experimental Biology, St. Louis, Mo.

Alternatively, a modification of the synthetic technique described in U.S. Pat. No. 4,211,867 may be employed. Thus, N-methylsuccinimide may be reduced with sodium borohydride in the presence of an alcohol of the formula $R^1OH$ where $R^1$ is alkyl of about 1 to 10 carbons such as ethyl at about $-10°$ C. followed by acidification to yield a 5-ether-substituted pyrrolidinone of the following formula (II):

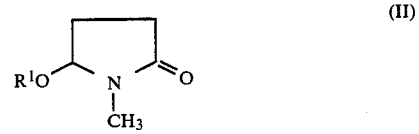

The ether (II) is then reacted at room temperature with the Meerwein reagent $Et_3OBF_4$ followed by addition of a guanidine of the following formula (III):

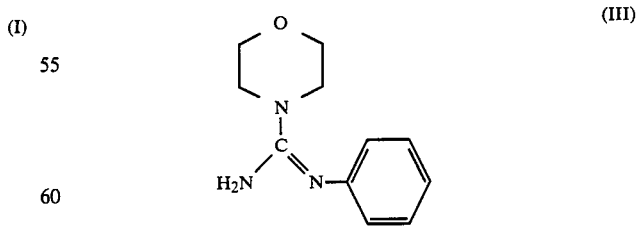

to yield a product of formula (I) wherein R is the value of $R^1$ used in the alcohol $R^1OH$. The compound of formula (III) may be prepared as described in U.S. Pat. No. 4,211,867 or in U.S. Serial No. 711,948 filed Mar. 15, 1985. To obtain the alcohol of formula (I) wherein R is hydrogen, the compound of formula (I), wherein R is $R^1$, is reacted at about room temperature with a strong acid such as 3N HCl. To obtain the derivative of formula (I) wherein R is alkanoyl, the hydroxy compound wherein R is hydrogen or the ether where R is $R^1$ may be reacted with a carboxylic acid at about room temperature in the presence of a strong acid such as hydrochloric acid.

The subject compounds (I) and salts thereof have been found to possess blood sugar lowering activity (i.e. hypoglycemic properties) as demonstrated in the following rat glucose tolerance test.

The rat glucose tolerance test is a standard and extremely sensitive procedure used in the diagnosis of diabetes and hypoglycemic disease states.

In this test, male Sprague-Dawley rats (Charles River 200–275 grams) are given water ad libitum and fasted 18–24 hours prior to the experiment. Three to five rats are randomly assigned to each test and control group. Test Compounds, 1–200 mg/kg, are administered (s.c., i.p. or orally) suspended in 0.5 or 1.0 milliliter, but preferably the former, of 0.5% (w/v) methylcellulose vehicle. Control animals are given an equal amount of vehicle. All drug doses are calculated as the free base. Serial blood samples (0.1 milliliter) are obtained from the tail without anesthesia prior to and at 30, 60, 90, 120, 150 and 180 minutes after administration of 0.8 to 1.0 gram of glucose per kilogram of body weight in 1 milliliter of water. (The glucose is given orally if the test compound has been given parenterally, and subcutaneously if the test compound has been given orally.) Specimens of blood are immediately deproteinized with aqueous solutions of $Ba(OH)_2$ and $ZnSO_4$ and glucose levels are determined using the glucose oxidase assay described by L. P. Cawley et al., "Ultra Micro Chemical Analysis of Blood Glucose with Glucose Oxidase", Amer. J. Clin. Path., 32, 195 (1959). The blood glucose values at each time point are expressed in terms of milligram percent (mg glucose/100 ml of blood). The mean glucose values of the controls are compared statistically by the Student's t-Test to the means of the experimental groups at each of the corresponding time points. If the compound lowers the blood glucose significantly at any time at a 95% confidence limit, the compound is considered to have hypoglycemic activity. The blood glucose lowering, expressed as percent lowering, is obtained by dividing the difference between the mean blood glucose values for test and control animals by the mean glucose value for the control animal.

In the rat glucose tolerance test, the compound of formula (I) wherein R is hydrogen produced in Example 2 was tested and produced a dose dependent (2.5 to 10 mg/kg of body weight subcutaneously) improvement of glucose tolerance with an $ED_{30}$ (dose which lowered blood glucose by 30% from control) equal to 4.0 mg/kg s.c. (95% confidence interval=3.6–4.4 mg/kg) compared to an $ED_{30}$ for linogliride of 6.1 mg/kg of body weight s.c. (95% confidence interval=4.3–8.1 mg/kg).

Pharmaceutical compositions of compounds of formula (I) may be prepared and used as known for the antidiabetic medicament linogliride.

To prepare the pharmaceutical compositions of this invention, one or more compounds or salt thereof of the invention as the active ingredient, is intimately admixed with a pharmaceutical carrier according to conventional pharmaceutical compounding techniques, which carrier may take a wide variety of forms depending on the form of preparation desired for administration, e.g. oral or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, color agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The phramaceutical compositions herein will contain, per dosage unit, e.g. tablet, capsule, powder, injection, teaspoonful and the like, from about 5 to about 500 mg of the active ingredient, and, preferably, from about 10 to about 300 mg.

In the treatment of diabetes, a compound of formula (I) may be administered in an amount of 10 to 2000 mg per day for an average human.

In the following examples and throughout the specification, the following abbreviations may be used: mg (milligrams); g (grams); mL (milliliters); L (liters); mmol (millimoles); M (molar); N (normal); EtOAc (ethyl acetate); EtOH (ethanol); THF (tetrahydrofuran); s.c. (subcutaneously); hr (hours); min (minutes); RT (room temperature); HPLC (high pressure liquid chromatography); NMR (nuclear magnetic resonance); m (multiplet); s (singlet); IR (infrared); and C, H, N, O etc. (the chemical symbols for the elements). Unless otherwise indicated, all temperatures are reported in °C. (degrees centigrade).

EXAMPLE 1

N-(5-Ethoxy-1-methyl-2-pyrrolidinylidene)-N'-phenyl-4-morpholinecarboximidamide Formula (I), $R=CH_2CH_3$ To a $-10°$ C. solution of N-methylsuccinimide (10.0 g, 88.4 mmol) in absolute EtOH (1.0 L), was added $NaBH_4$ (12.5 g, 330 mmol). The pH was maintained at 9 (broad range pH paper) by dropwise addition of 2N HCl in absolute EtOH over a period of 5 hr. After this time, excess $NaBH_4$ was destroyed over 30 min by addition of the above 2N HCl solution until pH=3. The reaction was then allowed to warm to 5° C. and stir for 1 hr. After neutralizing with ethanolic KOH, the solvent was removed in vacuo and the resulting residue was extracted with $CHCl_3$. Evaporation of the solvent gave the desired lactam in good purity as a colorless oil. This oil was dissolved in $CH_2Cl_2$ (100 mL) and alkylated by slow addition of $Et_3OBF_4$ L (90 mL, 1.0M in $CH_2Cl_2$, 90.0 mmol, Aldrich). After stirring at RT for 2 hr, N-morpholino-N'-phenylguanidine was added (neat, 16.3 g, 79.6 mmole) followed by $K_2CO_3$ (anhydrous, 12.2 g, 88.4 mmole). After stirring for 3 days, the reaction was partitioned between saturated aq. $NaHCO_3$ and $CH_2Cl_2$. The organic phase was then separated, dried ($MgSO_4$) and evaporated leaving a yellow oil.

Column chromatography (flash SiO$_2$; 20:30:1 CHCl$_3$/acetone/NH$_4$OH) gave 22.2 g of the ethoxy linogliride title compound as a pale yellow oil (76% yield).

EXAMPLE 2

N-(5-Hydroxy-1-methyl-2-pyrrolidinylidene)-N'-phenyl-4-morpholinecarboximidamide Formula (I), R=H The product of Example 1 was taken up in THF (200 mL) and 3N HCl (20 mL) was added. After stirring for 1 hr at RT, the reaction was quenched by addition to saturated NaHCO$_3$ and CH$_2$Cl$_2$. The aqueous phase was then brought to pH>12 with 3N NaOH. Extraction with CH$_2$Cl$_2$ (3×) followed by drying (MgSO$_{4L}$) and evaporation gave 16.2 g of pale yellow oil. Crystallization from EtOAc gave 2.80 g of the desired hydroxy linogliride. HPLC showed ~3% of the ethoxy linogliride. The mother liquor was purified by extracting the alcohol into 1N HCl, washing the aqueous phase with EtOAc, basifying with 3N NaOH and extracting with CH$_2$Cl$_2$. The CH$_2$Cl$_2$ fraction was then dried (MgSO$_4$) and evaporated leaving 6.2 g of solid material which was washed with EtOAc to give 5.13 g of fine white powder. HPLC showed >98% purity relative to ethoxy linogliride but NMR showed traces of CH$_2$Cl$_2$. The sample was slurried for 7 days in EtOAc and then filtered and dried under high vacuum (P$_2$O$_5$) for 3 days at 42° C. to give 3.66 g of the title product as a fine white powder which decomposed at about 150° C.

90 MHz NMR (CDCl$_3$; ppm); 7.20–6.60 (5H, m), 4.86–4.66 (1H, m), 3.76–3.33 (8H, m), 2.70 (3H, s), 2.26–1.25 L (4H, m). IR (KBr, cm$^{-1}$). 3085, 1641, 1547.

Elemental Analysis: Calculated: C, 63.56; H, 7.33; N, 18.52. Found: C, 63.63; M, 7.35; N, 18.52.

What is claimed is:

1. A 5-substituted pyrrolidinylidene of the following formula (I):

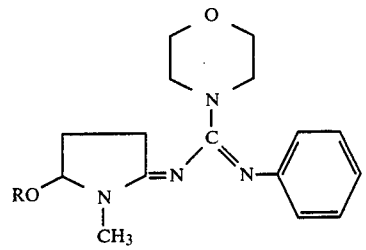

wherein R is alkyl or alkanoyl, and the pharmaceutically acceptable acid addition salts thereof.

2. The pyrrolidinylidene of claim 1, wherein R is alkyl.

3. The pyrrolidinylidene of claim 1, wherein R is alkanoyl.

4. The pyrrolidinylidene of claim 1, wherein R is alkyl of about 1 to 10 carbons.

5. The pyrrolidinylidene of claim 1, wherein R is alkanoyl of about 2 to 10 carbons.

6. The pyrrolidinylidene of claim 1, wherein said salt is a salt formed with an acid selected from the group consisting of hydrochloric, hydrobromic, sulfuric, nitric, phosphoric, acetic, propionic, glycolic, pamoic, pyruvic, malonic, succinic, maleic, fumaric, malic, tartaric, citric, benzoic, cinnamic, mandelic, methanesulfonic, ethanesulfonic, benzenesulfonic, p-toluenesulfonic, cyclohexanesulfamic, salicylic or p-aminosalicylic.

7. A pharmaceutical composition which comprises a pyrrolidinylidene of claim 1 in combination with a pharmaceutically acceptable diluent or carrier.

8. A method for the treatment of diabetes which comprises administering to a mammal in need thereof, the pharmaceutical composition of claim 7.

9. The method of claim 8, wherein said mammal is a human.

* * * * *